United States Patent [19]

Bell et al.

[11] Patent Number: 4,963,357

[45] Date of Patent: Oct. 16, 1990

[54] TISSUE PLASMINOGEN ACTIVATOR MODIFIED BY THE SUBSTITUTION OF ARG FOR CYS AT POSITION 73, METHODS AND PHARMACEUTICAL COMPOSITIONS THEREFOR

[75] Inventors: Leslie D. Bell, Chesterfield; Ernest J. Mayer, St. Louis; Mark O. Palmier, Webster Groves; H. Eser Tolunay, Creve Coeur; Thomas G. Warren, Ballwin; Tze-Chein Wun, St. Louis, all of Mo.

[73] Assignee: Monsanto Company, St. Louis, Mo.

[21] Appl. No.: 149,793

[22] Filed: Jan. 29, 1988

Related U.S. Application Data

[63] Continuation-in-part of Ser. No. 107,708, Oct. 9, 1987.

[51] Int. Cl.$^5$ .................. C12N 9/48; C12N 15/58; C12N 21/02; A61K 37/547
[52] U.S. Cl. .................. 424/94.64; 435/69.2; 435/172.3; 435/212; 435/226; 435/240.2; 435/320; 536/27; 935/10; 935/14; 935/23; 935/27; 935/70
[58] Field of Search .................. 435/212, 226, 240.2, 435/320, 235, 215; 935/14, 32, 70; 536/27; 424/94.64

[56] References Cited

U.S. PATENT DOCUMENTS 4,766,075  8/1988  Goeddel et al. .................. 435/212

FOREIGN PATENT DOCUMENTS

| 178105 | 4/1986 | European Pat. Off. |
| 227462 | 7/1987 | European Pat. Off. |
| 234051 | 9/1987 | European Pat. Off. |
| 242836 | 10/1987 | European Pat. Off. |
| 86/01538 | 3/1986 | PCT Int'l Appl. |
| 87/03906 | 7/1987 | PCT Int'l Appl. |
| 2173804 | 10/1986 | United Kingdom |

OTHER PUBLICATIONS

Wang, A. et al., *Science*, vol. 224, pp. 1431–1433, Jun., 1984.
Ny, T. et al., *Proc. Natl. Acad. Sci.*, vol. 81, pp.5355–5359, Sep., 1984.
Pennica et al., Nature 301, 214–221 (1983).
Vehar, Bio/Technology 2(12), pp. 1051–1057 (1984).
Kagitani et al., FEBS Lett. 189(1), 145–149 (1985).
Zonneveld et al., Proc. Natl. Acad. Sci. U.S.A. 83, 4670–4 (1986).
Verheijen et al., The EMBO J. 5(13), 3525–3530 (1986).
Ehrlich et al., Fibrinolysis 1, 75–81 (1987).
Klausner, Bio/Technology 4, 706–710 (1986).
Klausner, Bio/Technology 5, 869–870 (1987).
Lau et al., Bio/Technology 5(9) 953–958 (1987).

*Primary Examiner*—Richard A. Schwartz
*Assistant Examiner*—Larry Millstein
*Attorney, Agent, or Firm*—Scott J. Meyer; James W. Williams, Jr.

[57] ABSTRACT

A modified tissue plasminogen activator having an improved in vivo half-life characterized in that the normal protein moiety of 527 amino acids is mutated at the site Cys73→Arg.

12 Claims, 12 Drawing Sheets

```
<Cla I       >< Nde I                                                    ><
CGATAAGCTATGTCTTACCAAGTCATATGTAGAGACGAAAAGACTCAAATGATCTACCAACAACACCAATCTTGGTTGAG  80
TATTCGATACAGAAGTGTTCAGTATACATCTCTGCTTTCTGAGTTGAGTTTACTAGATGGTTGTTGTGGTTAGAACCAACTC
                        ><                                  ><                  ^
ACCAGTTTGCGTTCTAACAGAGTCGAATACTGTTGGTGTAACAGCCGGCCGCTCAATGTCACTCTGTTCCAGTCAAGT    160
TGGTCAAACGCAAGATTGTCTCAGCTTATGACAACCACATTGTCGGCCGGCCGAGTTACAGTGAGACAAGGTCAGTTCA
       ><                                   ><                       ><
CTTGTTCCGAACAAGATGTTCAACGGTGGTACTTGCCAACAGGCCTTGTATTCTCTGACTTCGTCTGTCAATGTCCA     240
GAACAAGGCTTGGTTCTACAAGTTGCCACCATGAACGGTTGTCCGGAACATAAAGAGACTGAAGCAGACAGTTACAGGT
         ^                     ><      Mlu I                             ><
GAAGGTTCGGCTGGTAAGTGTTGTGAAATCGACACGGGTGCTACTTGTTACGAAGACCAAGGTATTAGCTACAGAGGTAC  320
CTTCCAAAGCCGACCATTCACAACACTTTAGCTGTGCCCACGATGAACAATGCTTCTGGTTCCATAATCGATGTCTCCATG
    ><                                                          ><
CTGGTCTACCGCGGAATCTGGCCGCCGAATGTACCAACTGGAACTCTCCGCTTCCGCCAAAAGCCATACTCTGGTCGAC    400
GACCAGATGGCGCCTTAGACCGGCGGCTTACATGGTTGACCTTGAGAAGGCGAAAACCGGGTTTCGGTATGAGACCAGCTG
  ><                                     ><                     ><
GCCCAGACGCCATCAGATTGGGTTTGGTAATCACACTACTGTAGAAACCCGATCGTCGATTCTAAGCCTTGGTGTTAC    480
CGGGTCTGCGGTAGTCTAACCCAAACCATTAGTGTGATGACATCTTTGGGCTAGCACTAAGATTCGGAACCACAATG
    ><    ><EcoR I                                           ><
GTTTTCAAGGCTGGTAAATACTCTTCGAATTCTGTTCTACTCCAGCATGCTCTGAAGGTAACTCTGACTGTTACTTCGG   560
CAAAAGTTCCGACCATTTATGAGAAGCTTAAGACAAGATGAGGTCGTACGAGACTTCCATTGAGACTGACAATGAAGCC
                ><
```

FIG. 1A.

```
                                                                    Nco I
TAACGGTTCGCTTACAGAGGTACCCACTCGTTAACTGAATCTGGTGCTTCCTGTTGCCATGGAACTCTATGATCTTGA 640
ATTGCCAAGACGAATGTCTCCATGGGTCAGCAATTGACTTGACCACGAAGGACAAACGGTACCTTGAGATACTAGAACT

TTGGTAAGGTCTACACCGGCTCAAAACCCATCTGCTCAAGCCTTGGGTTTGGGTAAGCACAACTACTGTAGAAACCCAGAC 720
AACCATTCCAGATGTGGCGAGTTTGGGTAGACGAGTTCGGAACCCAAACCATTCGTGTTGATGACATCTTTGGGTCTG

GGTGACGCTAAGCCTTGGTGTCACGTTTTGAAGAACAGACGTCTACTTGGGAGTACTGTGACGTTCCCAGCTGTTCTAC 800
CCACTGCGATTCGGAACCACAGTGCAAAACTCTGTCTGCAAGAATGAACCCTCATGACACTGCAAGGGTCGACAAGATG
                                    Bgl II
CTGTCGGTTTGAGACAATACTCTCAACCACAATTCAGAATTAAAGTGGTTTATTCGCTGACATCGGAGCCATCCTTGGC 880
GACACCAAACTCTGTTATGAGAGTTGGTGTTAAGTCTTAATTTCCACCAAATAAGCGACTGTAGCGCTCGGTAGGAACCG

AAGCTGCCATCTTCGGCCAAGCACAGAGATCTCCAGTGAAGAAGATTCCCACCTCCACATTGACTGTTATCTTGGGTATTTTGATCAGCTCTCTTGTCC 960
TTCGACGGTAGAAGCCGGTTCGTGTCTTCTAGAGGTCCACTTCTAAGAACACACCCATAAAACTAGTCGAGAACAACC

ATTTTCTGCTGCCCACTGTTCCAAGAAGATTCCACCTCACCATTTGACTGTTATCTTGGGTAGAACCTACAGAGT 1040
TAAAACAGACGACGGGTGACAAAGGTTCTTTCTAAGGGTGGAGTTGGTAAACTGACAATAGAACCCATCTTGGATGTCTCA
   Ava I
CGTTCCCGGGCAAGAGGAAGAACAAAAGTTCGAAGTTCACAAGGAATTTGACGATGACACTTACCACA 1120
GCAAGGGCCCCTTCTCCTTCCTTGTTTCAAGCTTCAACTTTCATGTAGCAAGTGTTCCTTAAACTGCTACTGCTGAATGCTGT
```

*FIG. 1B.*

```
                                                                                                                         >< 1200
ACGATATCGCTTGTTACAATTGAAGTCTGACTCTTCCAGATGGCGCAAGAATCTTCCGTCGTTAGAACCCGTCTGTTG
TGCTATAGCGAACAATGTTAACTTCAGACTGAGAAGGTCTACGCCGTTCTTAGAAGGCAGCAATCTTGGCAGACAAAC
                           ><                                    ><
                                 Sac I                                    >< 1280
CCACCGGGCGACTTGCAATTGCCAGACTGGACTGAATGTGAGCTCTGTGGTTACGGTAAGCACGAAGCCTTGTCTCCATT
GGTGGCCCGCTGAACGTTAACGGTCTGACCTGACTTACACTCGAGACACCAATGCCATTCGTGCTTCGGAACAGAGGTAA
                                                                   ><Xba I
                                                                         >< 1360
CTACTCTGAAAGATTGAAGGAAGCTCACGTTAGATTGTACCCATCTCTAGATGTACCTCTCAACACTGTTGAACAGAA
GATGAGACTTTCTAACTTCCTTCGAGTGCAATCTAACATGGGTAGAGATCTACATGGAGAGTTGTGACAACTTGTCTT
                 ><                                  ><
                                                                         >< 1440
CTGTTACCGACAACATGTTGTGCTGGTGACACCCGTTCTGGTGGGCCCAAGCTAACTTGCACGACGCTTGTCAAGGT
GACAATGGCTGTTGTACAACACGACCACTGTGGGCAAGACCACCCGGGGTTCGATTGAACGTGCTGCGAACAGTTCCA
             ><                                   ><
                                                                         >< 1520
GACTCTCGGTGGTCCATTGGTCTGTTGAACGACGGTCGAATGACCTTGGTTGGTATCATTCTTGGGGTTTGGGTTGTGG
CTGAGACCACCAGGTAACCGACAGACAAACTTGCTGCCAGCTTACTGGAACCATAGTAAAGAACCCAAACCCAAACACC
                                                                    ><
                                                                Hind
                                                                       >< 1600
CCAAAAGGACGTTCCAGGTGTTTACACCAAGGTCACCAACTACTTAGACTGATCAGAGACAACATGAGACCATAATAAA
GGTTTTCCTGCAAGGTCCACAAATGTGGTTCCAGTGGTTGATGAATCTGACTGACTAGTCTCTGTTGTACTCTGGTATTATTT
                                    ><                             ><
III BamH I
GCTTG    1609
CGAACCTAG
```

*FIG. IC.*

```
        M  D  A  M  K  R  G  L  C  C  V  L  L  L  C  G  A
CGATAAGCTTGCAATCATGGATGCAATGAAGAGAGGGCTCTGCTGTGTGCTGCTGTGTGGAGCA
        V  F  V  S  P  S  Q  E  I  H  A  R  F  R  R  G  A  R--S  Y  Q  V  I
TATTCGAAGTTAGTACCTAGTTACTTCTCTCCGAGACACAGACACAGAGAGACACACCTCGT
GTCTTGTTTGCCCAGCCAGGAAATCCATGCCGATTCAGAAGCCGATCTTACCAAGTCA
CAGAAGCAAAGGGGTCGGTCCTTTAGGTACGGGCTAAGTCTTCTCCTCGGTCTAGAATGGTTCAGTAT
```

FIG. 2.

```
       GGATCCGGCGATAAGCTTGCAATCATGGATGCAATGAAGAGAGGGCTCTGCTGTGTGCTG
     1 ------------+----------+----------+----------+----------+ 60
       CCTAGGCCGCTATTCGAACGTTAGTACCTACGTTACTTCTCTCCCGAGACGACACACGAC
``` a:     GlySerGlyAspLysLeuAlaIleMetAspAlaMetLysArgGlyLeuCysCysValLeu -
                      -35

```
       CTGCTGTGTGGAGCAGTCTTCGTTTCGCCCAGCCAGGAAATCCATGCCCGATTCAGAAGA
    61 ------------+----------+----------+----------+----------+ 120
       GACGACACACCTCGTCAGAAGCAAAGCGGGTCGGTCCTTTAGGTACGGGCTAAGTCTTCT
``` a:     LeuLeuCysGlyAlaValPheValSerProSerGlnGluIleHisAlaArgPheArgArg -

```
       GGAGCCAGATCTTACCAAGTCATATGTAGAGACGAAAAGACTCAAATGATCTACCAACAA
   121 ------------+----------+----------+----------+----------+ 180
       CCTCGGTCTAGAATGGTTCAGTATACATCTCTGCTTTTCTGAGTTTACTAGATGGTTGTT
``` a:     GlyAlaArgSerTyrGlnValIleCysArgAspGluLysThrGlnMetIleTyrGlnGln -
               +1

```
       CACCAATCTTGGTTGAGACCAGTTTTGCGTTCTAACAGAGTCGAATACTGTTGGTGTAAC
   181 ------------+----------+----------+----------+----------+ 240
       GTGGTTAGAACCAACTCTGGTCAAAACGCAAGATTGTCTCAGCTTATGACAACCACATTG
``` a:     HisGlnSerTrpLeuArgProValLeuArgSerAsnArgValGluTyrCysTrpCysAsn -

```
       AGCGGCCGCGCTCAATGTCACTCTGTTCCAGTCAAGTCTTGTTCCGAACCAAGATGTTTC
   241 ------------+----------+----------+----------+---------- 300
       TCGCCGGCGCGAGTTACAGTGAGACAAGGTCAGTTCAGAACAAGGCTTGGTTCTACAAAG
``` a:     SerGlyArgAlaGlnCysHisSerValProValLysSerCysSerGluProArgCysPhe -

```
       AACGGTGGTACTTGCCAACAGGCCTTGTATTTCTCTGACTTCGTCCGTCAATGTCCAGAA
   301 ------------+----------+----------+----------+---------- 360
       TTGCCACCATGAACGGTTGTCCGGAACATAAAGAGACTGAAGCAGGCAGTTACAGGTCTT
``` a:     AsnGlyGlyThrCysGlnGlnAlaLeuTyrPheSerAspPheValArgGlnCysProGlu -
                      +73

```
       GGTTTCGCTGGTAAGTGTTGTGAAATCGACACGCGTGCTACTTGTTACGAAGACCAAGGT
   361 ------------+----------+----------+----------+---------- 420
       CCAAAGCGACCATTCACAACACTTTAGCTGTGCGCACGATGAACAATGCTTCTGGTTCCA
``` a:     GlyPheAlaGlyLysCysCysGluIleAspThrArgAlaThrCysTyrGluAspGlnGly -

```
       ATTAGCTACAGAGGTACCTGGTCTACCGCGGAATCTGGCGCCGAATGTACCAACTGGAAC
   421 ------------+----------+----------+----------+---------- 480
       TAATCGATGTCTCCATGGACCAGATGGCGCCTTAGACCGCGGCTTACATGGTTGACCTTG
``` a:     IleSerTyrArgGlyThrTrpSerThrAlaGluSerGlyAlaGluCysThrAsnTrpAsn -

*FIG. 5A.*

```
        TCTTCCGCTTTGGCCCAAAAGCCATACTCTGGTCGACGCCCAGACGCCATCAGATTGGGT
    481 ---------+---------+---------+---------+---------+---------+ 540
        AGAAGGCGAAACCGGGTTTTCGGTATGAGACCAGCTGCGGGTCTGCGGTAGTCTAACCCA
``` a:      SerSerAlaLeuAlaGlnLysProTyrSerGlyArgArgProAspAlaIleArgLeuGly -

```
        TTGGGTAATCACAACTACTGTAGAAACCCCGATCGTGATTCTAAGCCTTGGTGTTACGTT
    541 ---------+---------+---------+---------+---------+---------+ 600
        AACCCATTAGTGTTGATGACATCTTTGGGGCTAGCACTAAGATTCGGAACCACAATGCAA
``` a:      LeuGlyAsnHisAsnTyrCysArgAsnProAspArgAspSerLysProTrpCysTyrVal -

```
        TTCAAGGCTGGTAAATACTCTTCCGAATTCTGTTCTACTCCAGCATGCTCTGAAGGTAAC
    601 ---------+---------+---------+---------+---------+---------+ 660
        AAGTTCCGACCATTTATGAGAAGGCTTAAGACAAGATGAGGTCGTACGAGACTTCCATTG
``` a:      PheLysAlaGlyLysTyrSerSerGluPheCysSerThrProAlaCysSerGluGlyAsn -

```
        TCTGACTGTTACTTCGGTAACGGTTCTGCTTACAGAGGTACCCACTCGTTAACTGAATCT
    661 ---------+---------+---------+---------+---------+---------+ 720
        AGACTGACAATGAAGCCATTGCCAAGACGAATGTCTCCATGGGTGAGCAATTGACTTAGA
``` a:      SerAspCysTyrPheGlyAsnGlySerAlaTyrArgGlyThrHisSerLeuThrGluSer -

```
        GGTGCTTCCTGTTTGCCATGGAACTCTATGATCTTGATTGGTAAGGTCTACACCGCTCAA
    721 ---------+---------+---------+---------+---------+---------+ 780
        CCACGAAGGACAAACGGTACCTTGAGATACTAGAACTAACCATTCCAGATGTGGCGAGTT
``` a:      GlyAlaSerCysLeuProTrpAsnSerMetIleLeuIleGlyLysValTyrThrAlaGln -

```
        AACCCATCTGCTCAAGCCTTGGGTTTGGGTAAGCACAACTACTGTAGAAACCCAGACGGT
    781 ---------+---------+---------+---------+---------+---------+ 840
        TTGGGTAGACGAGTTCGGAACCCAAACCCATTCGTGTTGATGACATCTTTGGGTCTGCCA
``` a:      AsnProSerAlaGlnAlaLeuGlyLeuGlyLysHisAsnTyrCysArgAsnProAspGly -

```
        GACGCTAAGCCTTGGTGTCACGTTTTGAAGAACAGACGTCTTACTTGGGAGTACTGTGAC
    841 ---------+---------+---------+---------+---------+---------+ 900
        CTGCGATTCGGAACCACAGTGCAAAACTTCTTGTCTGCAGAATGAACCCTCATGACACTG
``` a:      AspAlaLysProTrpCysHisValLeuLysAsnArgArgLeuThrTrpGluTyrCysAsp -

```
        GTTCCCAGCTGTTCTACCTGTGGTTTGAGACAATACTCTCAACCACAATTCAGAATTAAA
    901 ---------+---------+---------+---------+---------+---------+ 960
        CAAGGGTCGACAAGATGGACACCAAACTCTGTTATGAGAGTTGGTGTTAAGTCTTAATTT
``` a:      ValProSerCysSerThrCysGlyLeuArgGlnTyrSerGlnProGlnPheArgIleLys -

FIG. 5B.

```
         GGTGGTTTATTCGCTGACATCGCGAGCCATCCTTGGCAAGCTGCCATCTTCGCCAAGCAC
     961 ------------------------------------------------------------ 1020
         CCACCAAATAAGCGACTGTAGCGCTCGGTAGGAACCGTTCGACGGTAGAAGCGGTTCGTG a:       GlyGlyLeuPheAlaAspIleAlaSerHisProTrpGlnAlaAlaIlePheAlaLysHis -

AGAAGATCTCCAGGTGAAAGATTCTTGTGTGGTGGTATTTTGATCAGCTCTTGTTGGATT
    1021 ------------------------------------------------------------ 1080
         TCTTCTAGAGGTCCACTTTCTAAGAACACACCACCATAAAACTAGTCGAGAACAACCTAA a:       ArgArgSerProGlyGluArgPheLeuCysGlyGlyIleLeuIleSerSerCysTrpIle -

TTGTCTGCTGCCCACTGTTTCCAAGAAAGATTCCCACCTCACCATTTGACTGTTATCTTG
    1081 ------------------------------------------------------------ 1140
         AACAGACGACGGGTGACAAAGGTTCTTTCTAAGGGTGGAGTGGTAAACTGACAATAGAAC a:       LeuSerAlaAlaHisCysPheGlnGluArgPheProProHisHisLeuThrValIleLeu -

GGTAGAACCTACAGAGTCGTTCCCGGGGAAGAGGAACAAAAGTTCGAAGTTGAAAAGTAC
    1141 ------------------------------------------------------------ 1200
         CCATCTTGGATGTCTCAGCAAGGGCCCCTTCTCCTTGTTTTCAAGCTTCAACTTTTCATG a:       GlyArgThrTyrArgValValProGlyGluGluGluGlnLysPheGluValGluLysTyr -

ATCGTTCACAAGGAATTTGACGATGACACTTACGACAACGATATCGCTTTGTTACAATTG
    1201 ------------------------------------------------------------ 1260
         TAGCAAGTGTTCCTTAAACTGCTACTGTGAATGCTGTTGCTATAGCGAAACAATGTTAAC a:       IleValHisLysGluPheAspAspAspThrTyrAspAsnAspIleAlaLeuLeuGlnLeu -

AAGTCTGACTCTTCCAGATGCGCGCAAGAATCTTCCGTCGTTAGAACCGTCTGTTTGCCA
    1261 ------------------------------------------------------------ 1320
         TTCAGACTGAGAAGGTCTACGCGCGTTCTTAGAAGGCAGCAATCTTGGCAGACAAACGGT a:       LysSerAspSerSerArgCysAlaGlnGluSerSerValValArgThrValCysLeuPro -

CCGGCCGACTTGCAATTGCCAGACTGGACTGAATGTGAGCTCTCTGGTTACGGTAAGCAC
    1321 ------------------------------------------------------------ 1380
         GGCCGGCTGAACGTTAACGGTCTGACCTGACTTACACTCGAGAGACCAATGCCATTCGTG a:       ProAlaAspLeuGlnLeuProAspTrpThrGluCysGluLeuSerGlyTyrGlyLysHis -

GAAGCCTTGTCTCCATTCTACTCTGAAAGATTGAAGGAAGCTCACGTTAGATTGTACCCA
    1381 ------------------------------------------------------------ 1440
         CTTCGGAACAGAGGTAAGATGAGACTTTCTAACTTCCTTCGAGTGCAATCTAACATGGGT a:       GluAlaLeuSerProPheTyrSerGluArgLeuLysGluAlaHisValArgLeuTyrPro -
```

*FIG. 5C.*

```
          TCTTCTAGATGTACCTCTCAACACTTGTTGAACAGAACTGTTACCGACAACATGTTGTGT
     1441 ------------------------------------------------------------ 1500
          AGAAGATCTACATGGAGAGTTGTGAACAACTTGTCTTGACAATGGCTGTTGTACAACACA a:     SerSerArgCysThrSerGlnHisLeuLeuAsnArgThrValThrAspAsnMetLeuCys -

GCTGGTGACACCCGTTCTGGTGGGCCCCAAGCTAACTTGCACGACGCTTGTCAAGGTGAC
     1501 ------------------------------------------------------------ 1560
          CGACCACTGTGGGCAAGACCACCCGGGGTTCGATTGAACGTGCTGCGAACAGTTCCACTG a:     AlaGlyAspThrArgSerGlyGlyProGlnAlaAsnLeuHisAspAlaCysGlnGlyAsp -

TCTGGTGGTCCATTGGTCTGTTTGAACGACGGTCGAATGACCTTGGTTGGTATCATTTCT
     1561 ------------------------------------------------------------ 1620
          AGACCACCAGGTAACCAGACAAACTTGCTGCCAGCTTACTGGAACCAACCATAGTAAAGA a:     SerGlyGlyProLeuValCysLeuAsnAspGlyArgMetThrLeuValGlyIleIleSer -

TGGGGTTTGGGTTGTGGCCAAAAGGACGTTCCAGGTGTTTACACCAAGGTCACCAACTAC
     1621 ------------------------------------------------------------ 1680
          ACCCCAAACCCAACACCGGTTTTCCTGCAAGGTCCACAAATGTGGTTCCAGTGGTTGATG a:     TrpGlyLeuGlyCysGlyGlnLysAspValProGlyValTyrThrLysValThrAsnTyr -

TTAGACTGGATCAGAGACAACATGAGACCATAATAAAGCTT
     1681 ----------------------------------------- 1721
          AATCTGACCTAGTCTCTGTTGTACTCTGGTATTATTTCGAA a:     LeuAspTrpIleArgAspAsnMetArgProEndEndSer??? -
```

FIG. 5D.

TISSUE PLASMINOGEN ACTIVATOR MODIFIED BY THE SUBSTITUTION OF ARG FOR CYS AT POSITION 73, METHODS AND PHARMACEUTICAL COMPOSITIONS THEREFOR

CROSS-REFERENCE TO RELATED APPLICATION

This is a continuation-in-part of copending application Ser. No. 107,708, filed Oct. 9, 1987.

BACKGROUND OF THE INVENTION

This invention relates to plasminogen activators which are useful thrombolytic agents. More particularly, this invention relates to a modified tissue plasminogen activator having an improved in vivo half-life.

It is known that various plasminogen activators (PA) are widely distributed throughout the body and can be purified from tissue extracts. Typical examples of tissue sources are kidney, lung and uterus tissues. The best characterized of these plasminogen activators fall into two major groups, urokinase plasminogen activator (u-PA) and tissue plasminogen activator (t-PA). u-PA and t-PA are present in ng/ml concentrations in human plasma but are immunologically unrelated. t-PA has been demonstrated to have higher affinity for fibrin than u-PA. u-PA products isolated and purified from human urine and from mammalian kidney cells are pharmaceutically available as thrombolytic agents.

Due to the extremely low concentration of t-PA in blood and tissue extracts, other sources and means of producing this preferred thrombolytic agent have been sought after.

One method of producing t-PA on a large scale comprises isolating the protein from the culture fluid of human melanoma cells grown under in vitro cell culture conditions. An established human melanoma cell line (Bowes) has been used for this purpose. See, for example, European Patent Application No. 41,766, published Dec. 16, 1981; Rijken and Collen, *J. Biol. Chem.* 256(13), 7035-7041 (1981); and Kluft et al., *Adv. Biotech. Proc.* 2, Alan R. Liss, Inc., 1983, pp. 97-110. The Bowes melanoma t-PA is a glycoprotein which has a molecular weight of about 68,000-70,000 daltons and a 527 amino acid structure with serine at the $NH_2$-terminus. The melanoma t-PA can exist as two chains, an A-chain and a B-chain. It also separates into two variants (or isoforms) in the A-chain, known as types I and II, which differ by about $M_r$ 2000-3000. See Ranby et al., *FEBS Lett.* 146 (2), 289-292 (1982), and Wallen et al., *Eur. J. Biochem.* 132, 681-686 (1983). Type I is glycosylated at Asn-117, Asn-184 and Asn-448 whereas Type II is glycosylated only at Asn-117 and Asn-448 according to Pohl et al., *Biochemistry* 23, 3701-3707 (1984). A high mannose structure has been assigned to Asn-117 whereas two complex carbohydrate structures are assigned to Asn-184 and Asn-448 by Pohl et al., "EMBO Workshop on Plasminogen Activators," Amalfi, Italy, Oct. 14-18, 1985.

Genetic information from the Bowes melanoma cell line also has been embodied in *E. coli* by conventional recombinant DNA gene splicing methods to permit the production of the t-PA protein moiety by that microorganism. See, for example, UK Patent Application No. 2,119,804, published Nov. 23, 1983; Pennica et al., *Nature* 301, 214-221 (1983); and Vehar et al., *Bio/Technology* 2 (12), 1051-1057 (1984). Recombinant t-PA produced by the expression of Bowes melanoma genetic material in cultured mammalian cells has been administered to humans with some measure of effectiveness. See Collen et al., *Circulation* 70(16), 1012-1017 (1984).

The recombinant-derived t-PA produced in *E. coli* is non-glycosylated and contains only the protein moiety of t-PA. Although the specific function of the carbohydrate moiety on t-PA has not been determined, it is known, in general, that glycosylation can cause certain differences of which the following are of biological interest: antigenicity, stability, solubility and tertiary structure. The carbohydrate side-chains also can affect the protein's half-life and target it to receptors on the appropriate cells. See, for example, Delente, *Trends in Biotech.* 3 (9), 218 (1985), and Van Brunt, *Bio/Technology* 4, 835-839 (1986). The functional properties of carbohydrate-depleted t-PA are further discussed by Little, et al., *Biochemistry* 23, 6191-6195 (1984), and by Opdenakker et al., "EMBO workshop on Plasminogen Activators," Amalfi, Italy, Oct. 14-18, 1985. The latter scientists report that enzymatic cleavage of carbohydrate side-chains from the melanoma (Bowes) derived t-PA by treatment with α-mannosidase causes an increase in the biologic activity of the modified t-PA.

Cultured normal human cells also have been used as a source of t-PA as can be seen from U.S. Pat. Nos. 4,335,215, 4,505,893, 4,537,860, and 4,550,080. Various cell sources mentioned in said patents are primary embryonic (or fetal) kidney, lung, foreskin, skin and small intestines (Flow Laboratories) or the AG1523 cell line. Brouty-Boye et al., *Bio/Technology* 2 (12), 1058-1062 (1984), further disclose the use of normal human embryonic lung cells for the production of t-PA. Rijken and Collen, *J. Biol. Chem.* 256(13), 7035-7041 (1981), and Pohl et al., *FEBS Lett.* 168(1), 29-32 (1984), disclose the use of human uterine tissue as a t-PA source material. European Patent Application No. 236,289, published Sept. 9, 1987, describes a uniquely glycosylated t-PA derived from normal human colon fibroblast cells.

Production of glycosylated t-PA in non-human mammalian cells also is known. Thus, Kaufman et al., *Mol. Cell. Biol.* 5, 1750-1759 (1985), and European Patent Application No. 117,059, published Aug. 29, 1984, describe the use of Chinese hamster ovary cells and Browne et al., *Gene* 33, 279-284 (1985), describe the use of mouse L cells for such production. Kaufman et al., state that the Chinese hamster ovary t-PA is glycosylated in a similar but not identical manner as native t-PA. Glycosylated forms of t-PA obtained by recombinant DNA are further described by Zamarron et al., *J. Biol. Chem.* 259 (4), 2080-2083 (1984), and Collen et al., *J. Pharmacol. Expertl. Therap.* 231 (1), 146-152 (1984).

Production of glycosylated t-PA by recombinant DNA yeast cells also has been reported. Thus, European Patent Application No. 143,081, published May 29, 1985, describes a recombinant yeast plasmid vector which encodes human t-PA from Hela cells. European Patent Application No. 174,835, published Mar. 19, 1986, describes a t-PA with selected glycosylation expressed in yeast in which the cDNA encoding for the t-PA is derived from Bowes melanoma. European Patent Application No. 178,105, published Apr. 16, 1986, discloses a glycosylated uterine t-PA expressed in yeast cells or mouse C-127 cells. In the latter case, a bovine papilloma virus is used as the vector.

Notwithstanding the great variety of sources for obtaining t-PA, one of the problems that exists with the normal t-PA molecule is its relatively short half-life. Intravenously administered t-PA disappears rapidly from the circulation into the liver where it is degraded. The half-life of this clearance is approximately 2 minutes in rabbits [Korninger et al., *Thromb. Haemostas.* 46, 658–661 (1981)]. Recent clinical studies have suggested that the half-life in humans may be slightly longer, on the order of 3–4 minutes [Nilson et al., *Scand. J. Haematol.* 33, 49–53 (1984)]. Since thrombolysis in vivo takes, at best, several hours to achieve, these findings indicate that the successful application of t-PA for thrombolysis in man will require its continuous infusion. Development of a t-PA with a longer half-life would allow for shorter periods of administration or a smaller dose.

Recently, so-called second generation type t-PAs have been prepared by recombinant DNA technology and various protein engineering schemes in attempting to improve the t-PA molecule. It is known that the normal t-PA molecule has five functional domains or regions: A fibronectin-like finger domain (F); an epidermal growth factor region (GF); two kringle regions (K1 and K2); and a serine protease region (SP). In the 527 amino acid sequence of the normal t-PA molecule described by Pennica et al., *Nature* 301, 214–221 (1983), the finger region comprises residues 1–43; the growth factor region comprises residues 44–91; kringle refers to a characteristic triple disulfide structure of which t-PA has two such regions, K1 - residues 92–173, and K2 - residues 180–261; and the serine protease comprises residues 262–527. The SP catalytic site is formed from the His-322, Asp-371 and Ser-478 residues. Various deletions of one or more of these regions together with elimination of one or more of the glycosylation sites such as by site-directed mutagenesis have been described heretofore. See, for example, Kagitani et al., *FEBS Lett* 189(1), 145–149 (1985); Zonneveld et al., *Proc. Natl. Acad. Sci. USA* 83, 4670–4674 (1986); Verheijen et al., *The EMBO J.* 5 (13), 3525–3530 (1986); Ehrlich et al., *Fibrinolysis* 1, 75–81 (1987); Klausner et al., *Bio/Technology* 4, 706–710 (1986) and 5, 869–870 (1987); and various abstracts in Thromb. Haemostasis. 58, 1–676 (1987). European Patent Application Nos. 234,051, published Sept. 2, 1987, and 242,836, published Oct. 28, 1987, and PCT International Application No. WO 87/03906, published July 2, 1987, disclose a variety of t-PA mutants having alterations in the arrangement or order of one or more of the functional domains.

Specific examples of t-PA having various other site-directed mutagenesis are as follows:

In European Patent Application No. 178,105, published Apr. 16, 1986, a modified t-PA is described in which one or more of the glycosylation sites have been eliminated by site-directed mutagenesis of Asn to Gln at the glycosylation sites in the kringle and serine protease regions. The amino acid residues Asn-120, -187 and -451 in the described uterine t-PA are equivalent to residues Asn-117, -184 and -448, respectively, in the Bowes melanoma t-PA. U.K. Patent Application No. G.B. 2,173,804, published Oct. 22, 1986, describes mutagenesis in the region of residues 270 to 279 to prevent conversion to the two-chain form of t-PA, especially mutagenesis of Arg-275 and Ile-276, e.g. Arg-275→Gly or Glu. In PCT International Application No. WO 86/01538, published Mar. 13, 1986, the mutant Lys-277→Ile is described. A variety of sitemutagens are also described in European Patent Application No. 227,462, published July 1, 1987, including mutagenesis at the above glycosylation sites and at the cleavage sites in the region 272–280, especially in the sequence Phe(274)-Arg(275)-Ile(276)-Lys(277).

BRIEF DESCRIPTION OF THE INVENTION

In accordance with the present invention a novel modified t-PA has been developed with a substantially improved in vivo half-life. These improved results were unexpected in view of the single site mutation of the native t-PA protein which characterizes the novel modified t-PA. For convenience, the modified t-PA of this invention can be represented as t-PA[Cys(73)→Arg]. In this mutation, a suggested disulfide bond at residue 73 is removed and a highly charged amino acid is substituted. This modification is likely to disrupt the local structure.

In a preferred embodiment, the modified t-PA was prepared from a chemically synthesized gene coding for t-PA with a single point mutation of Arg for Cys at residue 73. In this embodiment designated herein as t-PA variant MB1023, the mature protein has a 527 amino acid structure in which residue 73 is arginine instead of the cysteine that is present in native t-PA. This variant can be prepared by using an oligonucleotide sequence in the construction of the synthetic gene which codes for Arg instead of Cys at the appropriate position.

The gene coding for the modified t-PA of this invention can be cloned into and expressed in prokaryotic and eukaryotic hosts. For example, active modified t-PA protein can be expressed in a prokaryotic host such as *E. coli* or a eukaryotic host such as Chinese hamster ovary (CHO) cells or C-127 mouse cells by operably inserting the modified t-PA coding sequence in replicable expression vectors or plasmids. For example, it can be inserted into a suitable plasmid such as pML for production in *E. coli* and the bovine papilloma virus (BPV) vector for production in mouse cells or a shuttle vector which can replicate in both prokaryotic and eukaryotic cells. In a preferred embodiment, the gene coding for the t-PA sequence t-PA[Cys(73)→Arg] was cloned into and expressed from C-127 mouse cells. The excreted protein was extracted from the cell media by concentration and then purified on an affinity chromatography column.

A preferred cloning vector containing the nucleotide sequence for the t-PA variant MB1023 is plasmid pMON1401. This plasmid carried in a mouse C-127 host cell is on deposit with the American Type Culture Collection, Rockville, Md., under accession number ATCC CRL 9614. Other suitable eukaroytic and prokaryotic hosts for expression of the novel modified t-PA of this invention will be readily apparent to the person skilled in the art after reading the present disclosure.

The modified t-PA of this invention was shown to have a substantially longer half-life (t½) than native t-PA by injecting radiolabelled t-PA protein into rats. When measured in a plasminogen dependent rate assay or in an in vitro clot lysis assay, the modified t-PA was found to be less active than the native t-PA.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention in conjunction with the appended drawings, in which briefly:

FIG. 1 shows the construction of a chemically synthesized gene coding for t-PA assembled from individual oligonucleotides (positioned between the < > symbols) with nucleotide sequences and restriction enzyme sites as shown. Nucleotides are numbered on the right-hand side. The 1609 bp DNA of FIG. 1 is split into Panels A, B and C of FIG. 1.

FIG. 2 shows the nucleotide sequence of a synthetic gene fragment which includes the signal sequence of native t-PA. The 36 amino acids coded by the signal sequence beginning with methionine followed by the first 5 amino acids of the mature protein beginning with serine are shown above the nucleotide sequence.

FIG. 5 shows the nucleotide sequence of the t-PA variant MB1023 spread over 4 panels A, B, C and D. The nucleotides, which include some upstream and downstream processing, are numbered 1 to 1721 on the right-hand side. The corresponding amino acid sequence of the t-PA protein is shown below the nucleotide sequence in the rows labelled "a:" The signal sequence (as in FIG. 2) begins with the methionine at position −35 while the mature protein of 527 amino acids begins with the serine at position +1. An arginine is shown to replace the cysteine at position +73 of native t-PA.

Figure 6:
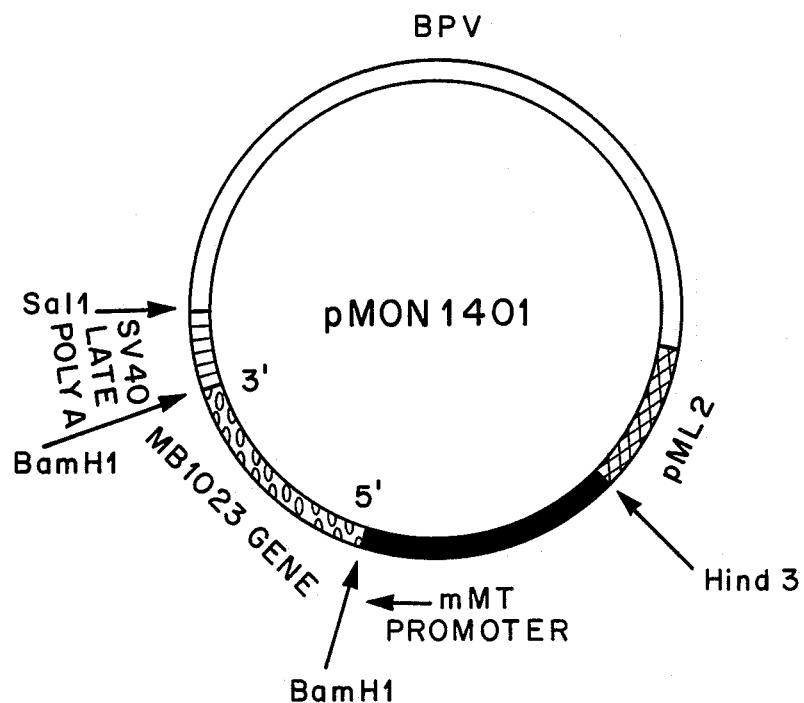

FIG. 6 shows the map of plasmid pMON1401 which is an expression vector for the expression of t-PA variant MB1023 in mouse C-127 cells in one embodiment of the invention. In this vector, BPV is the complete bovine papilloma virus genome, SV40 is the late poly(A) addition site of the SV40 virus, mMT is the mouse metallothionien I promoter and pML2 is a derivative of the E. coli plasmid pBR322 with an animal viral insert.

Figure 7:
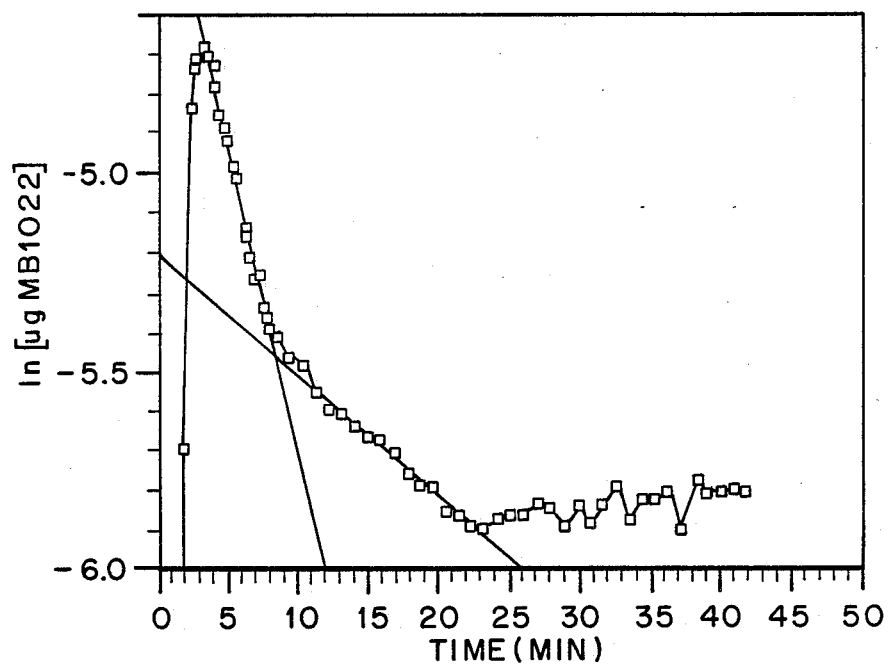

FIG. 7 is a graphical representation which shows the in vivo clearance of Bowes melanoma t-PA (MB1022) in the rat following bolus injection. The half-life (t½) was calculated by linear regression of ln [μg t-PA] vs. time (minutes).

Figure 8:
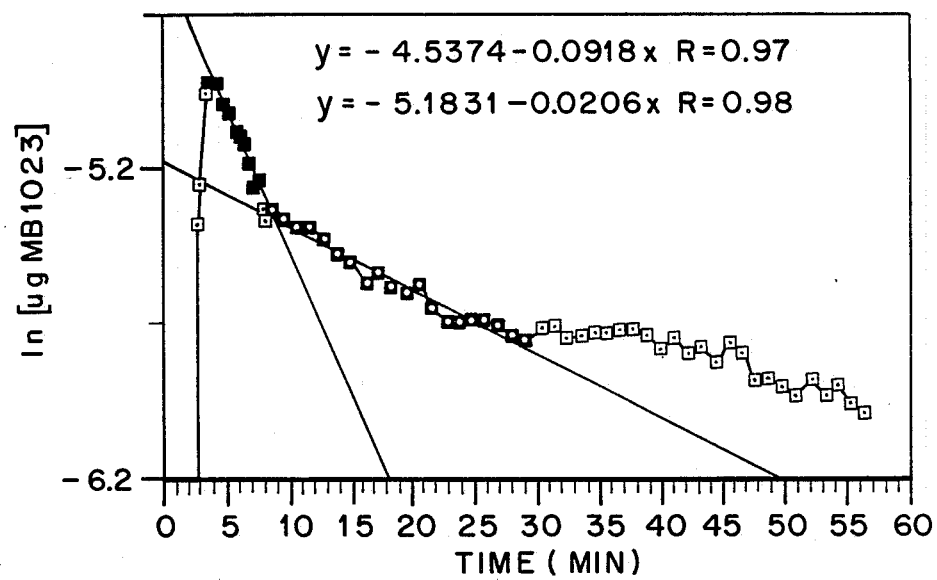

FIG. 8 is a graphical representation which shows the in vivo clearance of t-PA variant MB1023 in the rat following bolus injection. The t½ was calculated as in FIG. 7.

Figure 3:
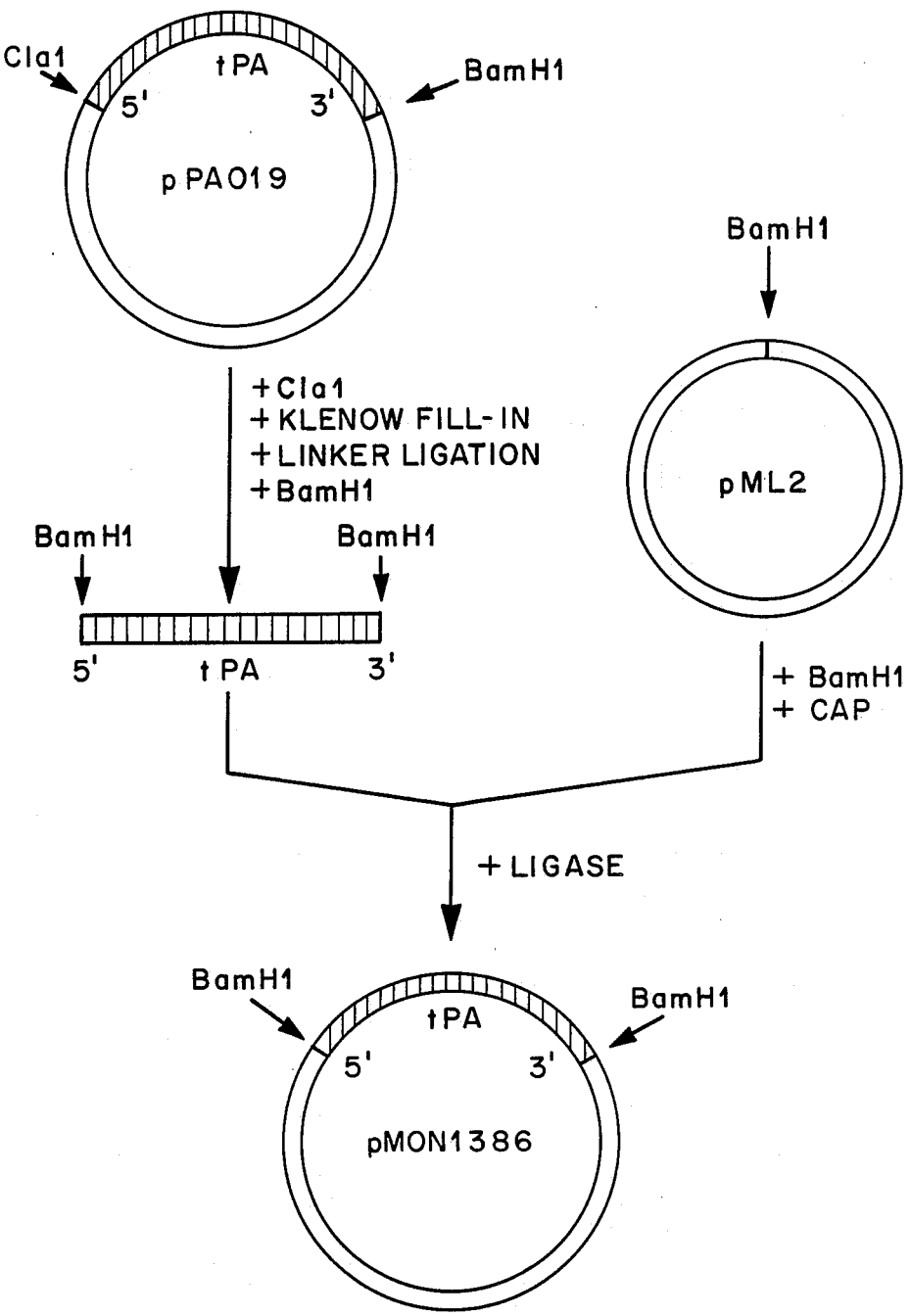
FIG. 3 shows the construction of plasmid pMON1386 of 4326 bp from plasmid pPA019 of 5028 bp and plasmid pML2 of 2600 bp.

The nucleotide sequences of FIGS. 1 and 2 and the construction of pMON1386 of FIG. 3 are also shown in co-pending application Ser. No. 107,708, filed Oct. 9, 1987.

Standard biochemical nomenclature is used herein in which the nucleotide bases are designated as adenine (A); thymine (T); guanine (G); and cytosine (C). Corresponding, nucleotides are, for example, deoxyadenosine-5'-triphosphate (dATP). Amino acids are shown either by three letter or one letter abbreviations as follows:

| Abbreviated Designation | Amino Acid |
|---|---|
| A | Ala | Alanine |
| C | Cys | Cysteine |

-continued

| Abbreviated Designation | | Amino Acid |
|---|---|---|
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Commonly available restriction endonucleases used herein have the following restriction sequences and (indicated by arrows) cleavage patterns.

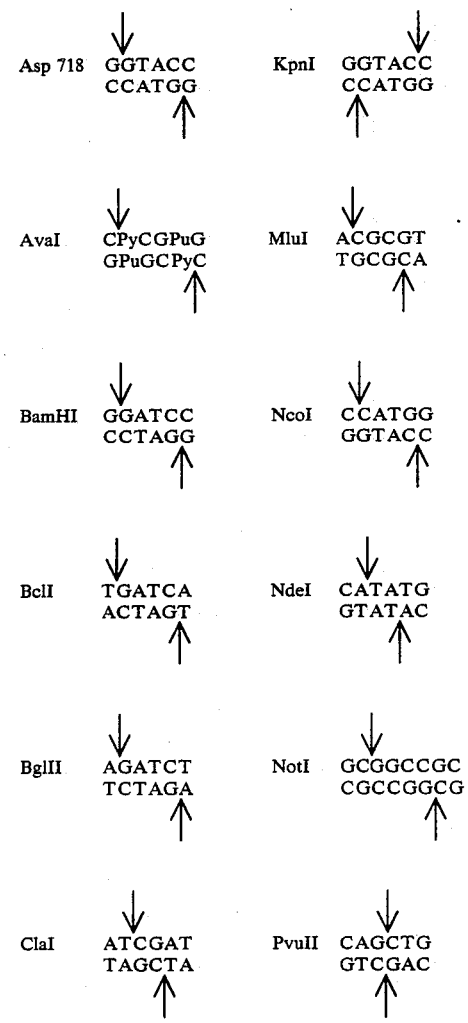

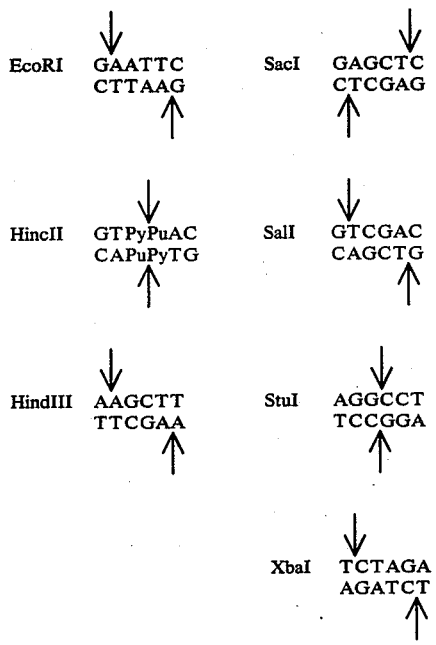

In order to illustrate specific preferred embodiments of the invention in further detail, the following exemplary laboratory work was carried out. This work includes the construction of a chemically synthesized t-PA gene from selected oligonucleotides and cloning of the gene in a suitable plasmid vector. The cloning and subsequent expression of a 527 amino acid modified t-PA (variant MB1023) having the protein sequence represented by t-PA[Cys(73)→Arg] is thus illustrated in detail.

EXAMPLES

CONSTRUCTION OF MB1023

MATERIALS

Enzymes were obtained from New England Biolabs, Boehringer Mannheim Biochemicals or Sigma Chemical Company and used according to the manufacturers printed specifications. Chemicals and components of media were obtained from Sigma Chemical Company and American Scientific Products, respectively. 5'-Dimethoxytritylated N-protected nucleosides were purchased from Cruachem. T4 DNA ligase and T4 polynucleotide kinase were obtained from Amersham International. Controlled pore glass (CPG, 700 Å A pore size, 200–400 mesh) was purchased from BDH.

METHODS

Construction of synthetic t-PA gene.

A synthetic t-PA gene was designed as shown in FIG. 1. The codon choice was based on optimum yeast codons, but also includes many restriction endonuclease sites. The gene was divided into oligonucleotides as shown, for the purpose of chemical synthesis.

Preparation of oligonucleotides

Aminopropyl CPG was prepared as described by Chow et al., *Nucleic Acids Research* 9, 2807–2817 (1981). 5'-Dimethoxytrityl deoxyribonucleoside 3'-O-succinates were synthesized and coupled to aminopropyl CPG following published procedures [Chow et al., Ibid.]. Methyl phosphodichloridite was prepared by the method of Martin and Pizzolato, *J. Amer. Chem. Soc.* 72, 4584–4586 (1950). 5'-Dimethoxytrityl-deoxyribonucleoside-3'-O-(N,N-diisopropylamino)-methyl phosphoramidites were prepared by a modification of the method of McBride and Caruthers, *Tetrahedron Letters* 24, 245–248 (1983). Products were precipitated from pentane at −20° C. and used without further purification. Phosphoramidites were stored at room temperature in a dry atmosphere. Oligonucleotides were prepared using an automated synthesizer. Syntheses were carried out in glass columns (bed volume: 6.5 mm I.D.×50 mm, Omnifit) containing 50 mg of derivatized CPG (25 μmole nucleotide/g). After each addition the yield was estimated by spectrophotometric assay of the acid-cleaved dimethoxytrityl cation. At the end of the synthesis the 5'-dimethoxytrityl group was removed by treatment with 3% dichloroacetic acid in dichloromethane. Other protecting groups were removed by treatment with thiophenol-dioxane-triethylamine (1:2:1) for 60 minutes at room temperature, followed by treatment with concentrated ammonia in a sealed vial at 70° C. for 4 hours.

Purification of oligonucleotides

Deprotected oligonucleotides were precipitated from concentrated ammonia by the addition of 0.1 volume of 3M sodium acetate (pH 5.2) and 2.5 volumes of ethanol. After 10 minutes at −70° C., the DNA was recovered by centrifugation. The pellet was washed with 80% ethanol, dried and redissolved in $H_2O$ (0.5 ml). An aliquot (20 $A_{260}$ units) was lyophilized and redissolved in formamide (25 μl) containing 0.01% bromophenol blue. The sample was heated for 2 minutes at 90° C. and then analyzed on a 15% denaturing gel (1.6 mm thick). After electrophoresis for 16 hours at 350V, products were visualized by UV shadowing. Oligonucleotides were eluted from the gel slices by soaking overnight in 0.5M ammonium acetate, 0.01M magnesium acetate, 0.1% sodium dodecylsulfate (SDS) (500 μl). The solution was filtered through 0.22 μm filters (Millipore) and the DNA recovered by ethanol precipitation. An aliquot of the purified oligonucleotide was analyzed on a denaturing gel after 5'-labelling with polynucleotide kinase and $^{32}P$-ATP.

Assembly of synthetic duplexes

With the exception of the two 5'-terminal oligonucleotides, aliquots of oligonucleotides (100–500 pmoles) were lyophilized and then phosphorylated in a mixture (20 μl) containing 0.1 mM $^{32}P$-ATP (5 μCi/mMole), 50 mM Tris-HCl, pH 7.6, 20 mM dithiothreitol (DTT), 0.1 mM spermidine and 2 units of T4 polynucleotide kinase. After 60 minutes at 37° C. phosphorylated oligonucleotides were isolated by electrophoresis on 15% denaturing gels. Oligonucleotides were eluted from gel slices as described above. Recovery was determined by Cerenkov counting of aliquots. Phosphorylated oligonucleotides (50 pmoles) were annealed in groups of 5. The oligonucleotides were combined and lyophilized, dissolved in $H_2O$ (15 μl), heated to 90° C. for 5 minutes and then slowly cooled to 20° C. Then 10×ligase buffer, 200 mM DTT and 10 mM ATP were added to give a final concentration of 50 mM Tris-HCl, pH 7.4, 10 mM $MgCl_2$, 20 mM DTT, 0.5 mM ATP. T4 DNA ligase (0.5 μl) was added. After 60 minutes at 20° C. the products were ethanol precipitated and analyzed on 10% native gels. Products were eluted as described above and aliquots (1%) were analyzed on denaturing gels. Synthetic oligonucleotides of defined sequence were used as size markers (93-mer, 72-mer, 57-mer, 49-mer, 41-mer, 35-mer).

Duplexes which contained products of the correct length were annealed at 50° C. and ligated together as described above. Products were isolated and analyzed in a similar manner.

Cloning of synthetic duplexes

All synthetic duplexes were initially cloned into the ClaI and BamHI sites of pAT153 (plasmid pPA019 in FIG. 3). The vector was prepared by digestion with ClaI and BamHI restriction endonucleases. After dephosphorylation with calf intestinal phosphatase (Boehringer), the 3.2 kbp fragment was purified by electrophoresis on a 1% agarose gel and recovered by electroelution.

Synthetic duplexes were phosphorylated before ligation to the vector. In a typical run, a 2:1 molar excess of vector:insert was used. Preparation of competent E. coli DH1 cells, transformation of cells and selection of ampicillin resistant colonies was carried out as previously described by Hanahan, J. Mol. Biol. 166, 557–580 (1983) and Maniatis et al., Molecular Cloning, A Laboratory Manual, Cold Spring Harbor Lab., N.Y., (1982).

Colonies were innoculated into L-broth (7 ml) containing L-ampicillin (100 μg/ml, Sigma) and grown up overnight at 37° C. An aliquot was removed for a glycerol stock and DNA was isolated from the remainder of the culture by the method of Holmes and Quigley, Anal. Biochem. 114, 193–197 (1981). Colonies containing the insert were identified by restriction enzyme analysis and colony hybridization, using oligonucleotides present in the synthetic gene.

Plasmid DNA for sequence analysis was obtained from larger cultures (500 ml) grown in the presence of chloramphenicol. DNA was isolated by a modification of the method of Clewell and Helinski, J. Bacteriology 110, 1135–1146 (1972), and purified on CsCl gradients. The sequence of the synthetic inserts was confirmed by the Maxam-Gilbert method, Methods in Enzymology 65, 499–560 (1980).

Figure 4:
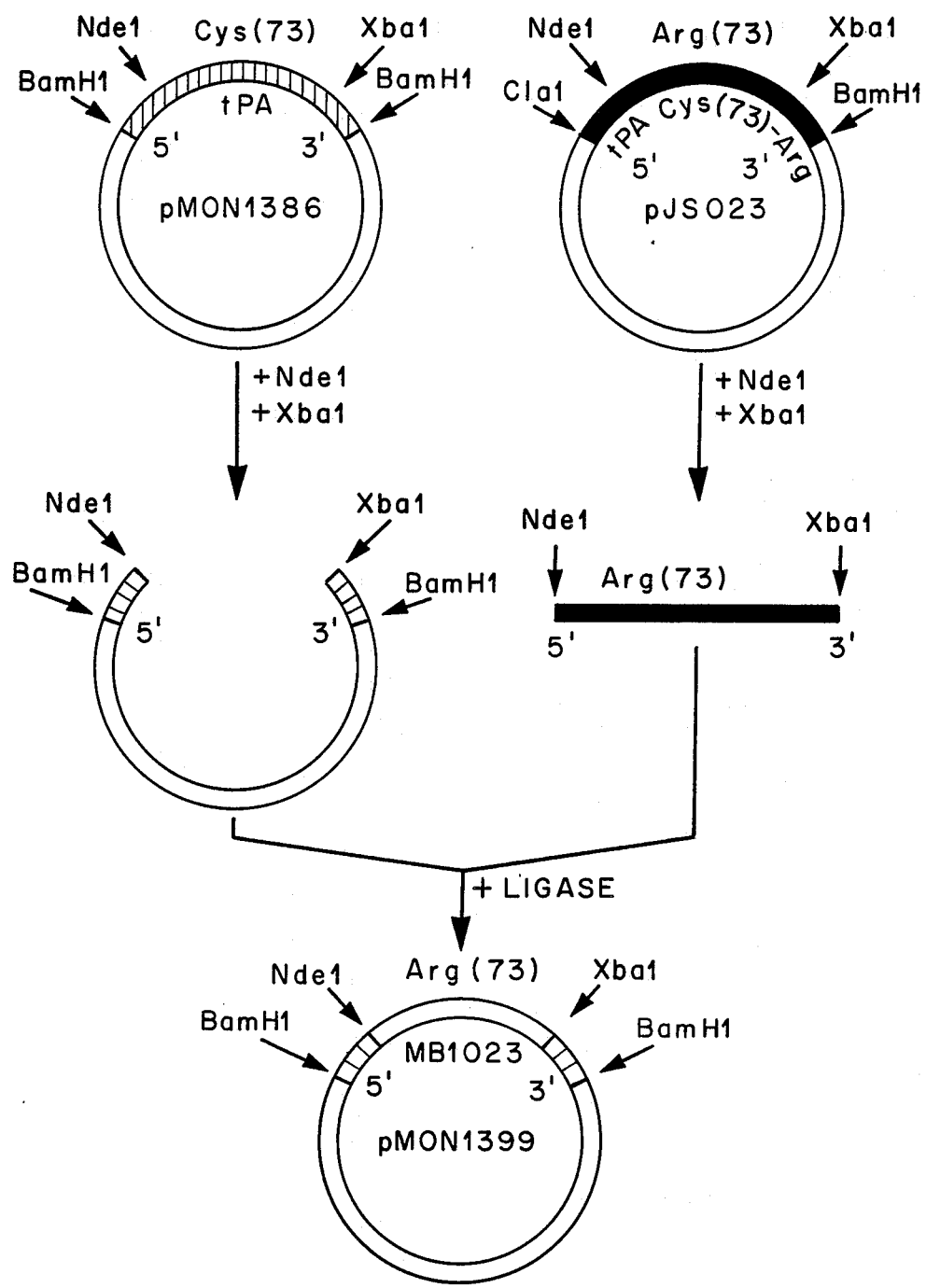
FIG. 4 shows the construction of plasmid pMON1399 from a large vector fragment cut from pMON1386 of FIG. 3 at its unique NdeI and XbaI sites and a 1300 bp fragment of the plasmid pJS023 containing a portion of the t-PA coding for Cys(73)→Arg.

Oligonucleotide PA95 (shown in FIG. 1 as the ninth oligonucleotide in the sequence - residues 217-244) was designed to have the sequence 5'TCTGACTTCGTCTGTCAATGTCCAGAAG 3'. Due to the side reactions that occur during the chemical synthesis the oligonucleotide PA95 was contaminated with the sequence 5'TCTGACTTCGTCCGTCAATGTCCAGAAG 3'. That is, the nucleotide 13 in the 28-mer was C instead of T. This resulted in the isolation and sequence analysis of a colony containing the mutation Cys(73)→Arg t-PA. The pAT153 derived plasmid containing this variant gene is designated pJS023 (FIG. 4). The variant protein derived from this gene is referred to as MB1023. This mutation can also be produced intentionally by substituting the appropriate oligonucleotides coding for arginine at the normal gene position corresponding to Cys(73).

A synthetic gene fragment coding for the natural signal sequence of t-PA (FIG. 2) was cloned into the ClaI - NdeI sites of the correct t-PA gene by methods described above to give the vector pPA019 (FIG. 3).

CONSTRUCTION OF A GENE CODING FOR MB1023

The gene and protein sequences of MB1023 are shown in FIG. 5. The signal sequence starts at amino acid position −35 (as shown) with the mature protein beginning at +1. An arginine residue is shown to replace the cysteine of native t-PA at position +73. Some upstream and downstream DNA sequence is present.

(A) Construction of pMON1386:

The 5'-ClaI site of pPA019 was converted to a BamHI site by the use of BamHI linkers as outlined in FIG. 3. Thus, pPA019 was digested with ClaI and the resulting 5'-overhanging ends were converted to blunt ends with Klenow fragment of DNA polymerase. BamHI linkers having the sequence 5'-CCGGATCCGG-3' (Pharmacia P-L Biochemicals) were then ligated onto these ends with T4 DNA ligase. After ligation the DNA was digested with BamHI and the resulting 1710 bp t-PA fragment was isolated using NA-45 DEAE membrane as described in Schleicher and Schuell technical literature 364. The purified fragment was then ligated into the BamHI site of the plasmid pML2. This mixture was used to transform E. coli HB101 cells to yield the plasmid pMON1386. Klenow fill-in reaction, ligation and transformation were done as described in Maniatis et. al., Molecular Cloning, A Lab. Manual, Cold Spring Harbor Laboratory, N.Y. (1982).

(B) Construction of pMON1399

A synthetic t-PA BamHI expression cassette possessing the Cys(73)→Arg change was constructed by exchange of NdeI-XbaI fragments between pMON1386 and pJS023 (FIG. 4). pMON1386 was digested at its unique NdeI and XbaI sites and the large vector fragment was isolated. Similarly pJS023 was digested with NdeI and XbaI and the 1300 bp fragment containing a portion of the t-PA coding region with the Cys(73-)→Arg change was isolated. The pJS023 NdeI-XbaI fragment was then ligated into the NdeI-XbaI cut pMON1386 to yield pMON1399. This plasmid contains the MB1023 Cys(73)→Arg t-PA with BamHI sites at the 5' and 3' ends of the synthetic gene.

Expression of MB1023

The t-PA variant MB1023 BamHI fragment was isolated by BamHI digestion of pMON1399. Following purification, this fragment was ligated into the unique BamHI site of the expression vector pMON1123 by reaction with T4 ligase using standard conditions [Maniatis et al. Molecular Cloning, A Lab. Manual, Cold Spring Harbor Laboratory, N.Y. (1982)]. The pMON1123 expression vector is based on the bovine papilloma virus/pML2 plasmid pPBV2308 (a gift of Dr. Dean Hamer, National Institutes of Health). pMON1123 was constructed by insertion of DNA fragments encoding the mouse metallothionien I promoter and the SV40 Late poly A addition site in such a way that these two fragments are separated by a unique BamHI site. DNA fragments inserted into this BamHI site are therefore expressed using the metallothionien promoter and SV40 Late poly A site regulatory signals. Insertion of the MB1023 BamHI fragment into pMON1123 yielded the plasmid pMON1401 (FIG. 6).

C-127 cells (mouse mammary tumor cells) (ATCC CRL 1616) were grown in high glucose Dulbecco's modified Eagles medium (DMEM) containing 5% heat-inactivated fetal bovine serum, 1X penicillinstreptomycin, and 1X glutamine. Twenty four hours prior to transfection, cells were seeded in 60 mm dishes at 4×10⁵ cells per dish. Cells were cotransfected with a mixture of pMON1401 and pSV2neo [Southern and Berg, *J. Molec. Appl. Genet.* 1, 327–341 (1982)] by the calcium phosphate precipitate method of Wigler et al, *Cell* 16, 777 (1979). Twenty four hours after transfection the 60 mm plates were each split 1:10 into 100 mm dishes containing high glucose DMEM, 5% heat-inactivated fetal bovine serum, 1X penicillin-streptomycin, 1X glutamine, and 50 KIU of aprotinin. This media was also supplemented with 800 μg/ml of the antiobiotic G418 (genticin) (GIBCO) for selection of neomycin resistant transfectants [Southern and Berg, supra]. After two weeks of selection G418 resistant colonies appeared These colonies were screened for M1023 production by the use of a fibrin overlay screen performed essentially by the method of Cederholm-Williams et al., in "Treatment of Metastasis: Problems and Prospects," Hellman and Eccles, Eds. (Taylor and Francis, London and Philadelphia) pp. 347–350 (1985). Each plate was overlayed with a 1.2% agarose matrix containing Dulbecco's minimal Eagles medium, 0.1 U/ml bovine thrombin (CalBiochem), 3 mg/ml bovine fibrinogen (CalBiochem), and 0.07/ml human plasminogen (Kabi). Following incubation at 37° C., clearing zones in the fibrin matrix appeared over specific colonies. These colonies were picked and seeded into wells of 24 well plates. Each well was allowed to grow to confluency and then expanded into a T75 flask to establish a stable line. The expression level of these lines was monitored by a t-PA specific ELISA (American Diagnostica).

The cell line having the highest expression levels was expanded into multiple T75 flasks. These cells were used to seed a 6000 cm² cell factory (Nunc). The cells were allowed to proliferate in the normal growth media until confluent. At this time the cells were washed with phosphate buffered saline containing Ca$^{+2}$ and Mg$^{+2}$ and were then fed with serum-free DMEM containing 2X penicillin-streptomycin, 1X glutamine, 50 KIU/ml aprotinin, and 0.3% lactalbumin hydrolysate. Conditioned media was replaced with fresh media every 3 days and used for protein purification.

MB1023 isolation

Purification of MB1023 was achieved by affinity chromatography on an Erythrina inhibitor-Sepharose® 4B column [Heussen et al, *J. Biol. Chem.* 259, 11635–11638 (1984)]. The conditioned medium was concentrated by ultrafiltration on Amicon's YM 30 spiral membrane system. The concentrates were made up to 0.5M NH₄HCO₃, 1% Triton X-100 and centrifuged at 26,000×g for 1 hr. The supernatant was then loaded onto an Erythrina inhibitor-Sepharose 4B column (6×2.5 cm). The column was washed with 300 ml of 0.5M NH₄HCO₃, 1% Triton X-100 and then with 50 mM NH₄HCO₃ until detergent free. The bound MB1023 was then eluted with 2.5M KSCN, 50 mM Na₃PO₄, pH 7.3. The eluted MB1023 was then dialyzed extensively against 1M NH₄HCO₃. The whole purification process was carried out at 4° C.

Amino Acid sequence analysis

Automated Edman degradation chemistry was used to determine the NH₂-terminal protein sequence. An Applied Biosystems, Inc., model 470A gas phase sequencer (Foster City, Calif.) was employed for the degradation [Hunkapiller et al., *Methods Enzymol* 91, 399–413 (1983)]. The respective PTH-aa derivatives were identified by RP-HPLC analysis in an on-line manner employing an Applied Biosystems, Inc., Model 120A PTH Analyzer fitted with a Brownlee 2.1 mm I.D. PTH-C18 column.

Protein determination

The protein concentration of MB1023 was determined by measuring absorbance at 280 nm and assuming that a concentration of 1 mg/ml gives an absorbance of 1.75.

Assays of enzymatic activity

The amidolytic activity of MB1023 was measured using a synthetic substrate, S-2288 (H-D-isoleucyl-L-propyl-L-arginine-p-nitroanilide). The reaction mixture contains 10 μl of 20 μg/ml MB1023 in PBS, 5 mg/ml BSA, 2.5 mg/ml bovine gamma globulin, 10 μl of 0.01M S-2288, and 230 μl of 0.1M Tris-HCl, pH 8.7, 0.5% Triton X-100. Amidolysis was followed by measuring the absorbance change with time at 405 nm.

The plasminogen activator activity of MB1023 was determined by a parabolic rate assay system as follows: Standard t-PA (0–15 I.U/ml) or MB1023 were prepared in a PBS solution containing 5 mg/ml BSA and 2.5 mg/ml bovine gamma globulin (PBB). Twenty μl of the t-PAs were mixed with 20 μl of human fibrinogen (2 mg/ml in 0.15M NaCl) in microfuge tubes and placed on ice. To each tube was added 60 μl of a reaction cocktail which consisted of 20 μl of P-buffer (0.25M Tris-HCl, pH 7.35, 0.5M NaCl, 25 mM EDTA), 5 μl of 3 mg/ml plasminogen, 5 μl of S-2251 (H-D-Val-Leu-Lys-p-nitroanilide), 5 μl of 20 U/ml human thrombin, 1 mg/ml BSA, and 25 μl H₂O. These were kept on ice until the cocktail was added to all the tubes. The tubes were then transferred to a water bath and incubated at 37° C. for 1.5 hr. To stop the reaction, 0.2 ml of 10% acetic acid was added to each tube. After a brief vortexing and centrifugation, the supernatants were transferred to a 96-well plate for absorbance measurement at 410 nm using a control (without added t-PA) as reference. The activity of the t-PA MB1023 was determined by comparing the $A_{410}$ with that of standard t-PA.

In this assay, it was found that a batch of melanoma single-chain t-PA obtained from American Diagnostica (lot 47-10) has a specific activity of 769±21 I.U./ug using WHO t-PA standards as reference. Because of limited supply of WHO standard, American Diagnostica's t-PA (lot 47-01) was subsequently used as the standard.

Plasma clot lysis assay

The standard t-PA and MB1023 induced plasma clot lysis assay was performed essentially as described by Wun and Capuano, *J. Biol. Chem.* 260, 5061–5066 (1985). In brief, plasma was supplemented with $^{125}$I-fibrinogen and 0.02% NaN₃ and divided into 95 μl aliquots in microfuge tubes. Five μl of a solution containing 100 NIH units/ml of thrombin and various amounts of standard t-PA or MB1023 were added to each microfuge tube. The clots were incubated at 37° C. At various time intervals a tube was taken, vortexed, and centrifuged to separate the serum. The percent of clot lysis was calculated based on the amount of $^{125}$I- fibrin degradation products released into serum.

Preparation of $^{125}$I-t-PAs

Iodination of t-PAs was carried out by the Iodo-Bead (Pierce) method [Markwell, *Anal. Biochem.* 125, 427–432(1982)]. Ninety μl of MB1023 (1.0 mg/ml) was mixed with an Iodo-Bead and 5 μl of Na¹²⁵I (0.5 mCi) and incubated at room temperature for 8 min. Then, the mixture was chromatographed on a 5 ml Sephadex G25 (fine) column pre-equilibrated in 1M NH₄HCO₃. Fractions of 0.2 ml were collected and the radioactive protein peak was pooled and dialyzed against 1M NH₄HCO₃.

In vivo clearance of t-PAs in rat

Wistar rats (~300 g) were anesthetized by intraperitoneal injection of sodium pentobarbital. The rat was then cannulated at the right jugular vein and carotid artery using polyethylene tubing (I.D. 0.58 mm; O.D. 0.97 mm). The cannula of the carotid artery was connected to silicon tubing (I.D. 0.63 mm; O.D. 1.2 mm) which feeded through a larger tubing (I.D. 1.3 mm; O.D. 3.3 mm) of a microperpex peristaltic pump (LKB). Blood was collected into a fraction collector. A heparin solution was injected through the jugular vein such that the concentration in circulation was approximately 2 units/ml, assuming that the blood volume is 7 ml per 100 g body weight. After 5 min., 15 μg of ¹²⁵I-t-PA was injected through the jugular vein and the blood was pumped into fraction collector at a speed of 30 μl/fraction/20 sec initially, and at 30 μl/fraction/60 sec after 25 fractions were collected. The time course of the clearance of MB1023 is followed by counting the radioactivity in each fraction of blood collected. Half-life of MB1023 was calculated by linear regression of ln (t-PA) vs. time, The half-life ($t_{\frac{1}{2}}$) was calculated from the formula $$t_{\frac{1}{2}} = \frac{\ln 0.5}{S},$$

S being the slope of the regression line.

Rabbit jugular vein thrombolysis assay

Clot lysis in vivo was studied using a rabbit jugular vein thrombolysis model as described by Collen et al., *J. Clin. Invest.* 71, 368–376 (1983).

ASSAY RESULTS

Isolation of MB1023

The C-127 cells transfected with MB1023 gene were grown in culture and the serum-free conditioned medium was collected for purification of MB1023 using Erythrina inhibitor Sepharose 4B as described above. From 8 L of medium, 33 mg of MB1023 was isolated.

Enzymatic activity of MB1023

The enzymatic properties of the MB1023 were assessed by a number of assays and compared to melanoma t-PA (MB1022). In the amidolytic assay system described above, both MB1022 and MB1023 t-PAs gave a rate of absorbance change of 0.0148 units/min.

In the parabolic rate assay, consisting of fibrin-plasminogen-S2251 and t-PAs, the MB1022 possesses a specific activity of 769 I.U./μg. In comparison, the MB1023 has a specific activity of 53 I.U./μg.

In the plasma clot lysis assay, the concentration of MB1023 required to lyse 50% of the clot in 4 hr at 37° C. is 106 ng/ml, in comparison to that for MB1022 t-PA which requires 17 ng/ml. These in vitro data suggest that MB1023 has 6–14 fold decrease in fibrin-specific activity compared to MB1022 t-PA.

Clearance of MB1023 in the rat

As shown in FIG. 7, the clearance of melanoma t-PA MB1022 in the rat after bolus injection follows biphasic kinetics with an initial rapid decline ($t_{\frac{1}{2}}$ alpha=4.4±0.1 min, n=3) followed by a slower decline ($t_{\frac{1}{2}}$ beta=19±3 min, n=2). In comparison, MB1023 shows an $t_{\frac{1}{2}}$ alpha=7.9±0.4 min and $t_{\frac{1}{2}}$ beta=28±7 min. (n=2). (FIG. 8).

Thrombolysis in rabbit

Thrombolysis was performed using a rabbit jugular vein model either by infusion of t-PAs over a 4 hour period and measuring the lysis at 4.5 hr or by a bolus injection over 10 min and measuring the lysis at 2 hr. In the infusion study, lysis was 88±1% (n=2) at 1 mg/kg, 67±9% (n=5) at 0.5 mg/kg, and 41±16% (n=2) at a 0.25 mg/kg for control C127 t-PA; and 76±18% (n=4) at 0.5 mg/kg for MB1023. In the 10 min bolus injection study, lysis after 2 hr was 57% (n=1) for control C127 t-PA and 86±0% (n=2) for MB1023, both at 0.5 mg/kg dose. These studies indicate that MB1023 is more thrombolytic than the control C127 t-PA.

The modified t-PA of the invention can be used for the treatment of thrombolytic conditions by suitable administration to a patient in need of such treatment. The amount of the t-PA which would normally be administered is primarily dependent upon the physical characteristics of the recipient and the severity of the thrombolytic condition. The amount to be administered must be an effective amount, that is, an amount which is medically beneficial but does not present toxic effects which overweigh the advantages which accompany its use. The preferable route of administration is parenteral, especially intravenous. Intravenous administration of the t-PA in solution with normal physiologic saline is illustrative. Other suitable formulations of the active t-PA in pharmaceutically acceptable diluents or carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention and it is intended that all such other examples be included within the scope of the appended claims.

What is claimed is:

1. A modified human tissue plasminogen activator having an improved in vivo half-life, the modification consisting of the substitution of arginine for cysteine at the position corresponding to position 73 in the 527 amino acid sequence of native human t-PA.

2. A modified human tissue plasminogen activator consisting of the amino acid sequence shown in FIGS. 5A, 5B, 5C and 5D.

3. An isolated, purified DNA sequence coding for the modified tissue plasminogen activator of claim 1.

4. An isolated, purified DNA sequence coding for the modified tissue plasminogen activator of claim 2.

5. An isolated, purified tissue plasminogen activator gene having the nucleotide sequence shown in FIGS. 5A, 5B, 5C and 5D.

6. A cloning vector comprising the DNA sequence of claim 3.

7. A cloning vector comprising the DNA sequence of claim 4.

8. A cloning vector comprising the tissue plasminogen activator gene of claim 3.

9. Plasmid pMON1401.

10. Mouse C-127 cells transformed with the plasmid of claim 9.

11. A process for preparing a modified human tissue plasminogen activator having an improved in vivo half-life, the modification consisting of the substitution of arginine for cysteine at the position corresponding to position 73 in the 527 amino acid sequence of native human t-PA which comprises culturing under conditions sufficient to produce said tissue plasminogen activator a host cell which has been transformed with recombinant DNA coding for said modified tissue plasminogen activator.

12. A pharmaceutical composition comprising the modified human tissue plasminogen activator of claim 1 and a pharmaceutically acceptable diluent or carrier.

* * * * *